United States Patent [19]

Adler et al.

[11] Patent Number: 5,049,582
[45] Date of Patent: Sep. 17, 1991

[54] PROSTACYCLIN DERIVATIVES WITH CYTOPROTECTIVE EFFECT ON LIVER, PANCREAS AND KIDNEY

[75] Inventors: Guido Adler; Rolf Schulte-Hermann, both of Marburg; Olaf Loge, Berlin, all of Fed. Rep. of Germany

[73] Assignee: Schering Aktiengesellschaft, Berlin and Bergkamen, Fed. Rep. of Germany

[21] Appl. No.: 315,878

[22] Filed: Feb. 27, 1989

Related U.S. Application Data

[63] Continuation of Ser. No. 862,359, May 12, 1986, abandoned.

[30] Foreign Application Priority Data

Jul. 25, 1984 [DE] Fed. Rep. of Germany ....... 3427797

[51] Int. Cl.$^5$ .................... A61K 31/19; A61K 31/34
[52] U.S. Cl. .................................. 514/469; 514/573; 514/893
[58] Field of Search ................ 514/469, 573

[56] References Cited

U.S. PATENT DOCUMENTS

| | | | |
|---|---|---|---|
| 4,219,479 | 8/1980 | Vorbrüggen et al. ............. | 424/263 |
| 4,464,388 | 8/1984 | Sakai et al. ....................... | 424/275 |
| 4,503,068 | 3/1985 | Sakai et al. ....................... | 514/412 |

FOREIGN PATENT DOCUMENTS 1181747 1/1985 Canada .

OTHER PUBLICATIONS

Chemical Abstracts 92:122181e (1980) (Araki et al).

*Primary Examiner*—Leonard Schenkman
*Attorney, Agent, or Firm*—Millen, White & Zelano

[57] ABSTRACT

The invention relates to an agent for cytoprotection in the liver, in the pancreas and in the kidney, characterized in that it contains prostacyclin derivatives of Formula I

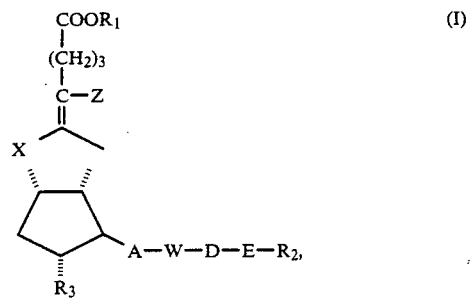

wherein
$R_1$ is hydrogen or alkyl of 1–10 carbon atoms,
A is a $-CH_2-CH_2-$, trans-$CH=CH-$ or $-C\equiv C-$ group,
W is a free hydroxymethyl group or a hydroxymethyl group functionally modified at the hydroxy group, the OH-group being in the $\alpha$- or $\beta$-position,
X is a $CH_2$-group or an oxygen atom,
Z is hydrogen or a cyano group,
D is a straight-chain or branched saturated alkylene group of 1–5 carbon atoms,
E is a $-C\equiv C-$bond or a direct bond,
$R_2$ is a straight- or branched-chain, saturated alkyl group of 1–7 carbon atoms,
$R_3$ is a free or functionally modified hydroxy group,
and, if $R_1$ means a hydrogen atom, the salts thereof with physiologically compatible bases,
and to a process for the preparation of the aforementioned agents.

4 Claims, 6 Drawing Sheets

PROSTACYCLIN DERIVATIVES WITH CYTOPROTECTIVE EFFECT ON LIVER, PANCREAS AND KIDNEY

This is a continuation of application Ser. No. 06/862,359 filed May 12, 1986, now abandoned.

The present invention relates to an agent with cytoprotective effect on liver, pancreas and kidney containing prostacyclin derivatives as the active medium, as well as to a process for the production of these agents.

The cytoprotective effect of carbacyclin derivatives on gastric and intestinal mucosa, as well as the myocardial cytoprotection with the aid of carbacyclin derivatives have been known from EP 11,591.

DESCRIPTION OF THE DRAWINGS

FIGS. 1A–1E are histologic sections of the pancreas of rats illustrating the morphology of cultivated hepatocyes wherein FIG. 1A is the control culture; FIGS. 1B and 1C are sections after the addition of $CCl_4$ (0.12 $\mu l/ml$) while simultaneously adding Iloprost (0.2 ng/ml) in an aqueous solution. The photographs of FIGS. 1A–1E are phase contrast photographs, 66×.

In FIGS. 3 and 4 the average value and standard deviation of respective 2–3 cultures are indicated; the significance of the differences was analyzed according to student's t test.

\* $p < 0.5$; \*\* $p < 0.1$

— No $CCl_4$ + $CCl_4$ (0.35 $\mu l/ml$)

It has now been found that prostacyclin derivatives of general Formula I wherein
$R_1$ is hydrogen or alkyl of 1–10 carbon atoms,
A is a $-CH_2-CH_2-$, trans-$CH=CH-$ or $-C\equiv C-$group,
W is a free hydroxymethyl group or a hydroxymethyl group functionally modified at the hydroxy group, the OH-group being in the $\alpha$- or $\beta$-position,
X is a $CH_2$-group or an oxygen atom,
Z is hydrogen or a cyano group,
D is a straight-chain or branched saturated alkylene group of 1–5 carbon atoms,
E is a $-C\equiv C-$bond or a direct bond,
$R_2$ is a straight- or branched-chain, saturated alkyl group of 1–7 carbon atoms,
$R_3$ is a free or functionally modified hydroxy group, and, if $R_1$ means a hydrogen atom, the salts thereof with physiologically compatible bases, exhibit cytoprotective effectiveness also in the liver, in the pancreas and in the kidney.

The alkyl group $R_1$ is considered to be straight or branched alkyl groups of 1–10 carbon atoms, such as, for example, methyl, ethyl, propyl, butyl, isobutyl, tert-butyl, pentyl, neopentyl, heptyl, hexyl, decyl. The alkyl groups $R_1$ can be optionally substituted by halogen atoms, $C_1$-$C_2$-alkoxy groups, phenyl or ($C_1$-$C_2$)-dialkylamines.

Examples for substituents are fluorine, chlorine or bromine atoms, phenyl, dimethylamine, diethylamine, methoxy, ethoxy. Preferred alkyl groups $R_1$ that can be named are those of 1–4 carbon atoms, such as, for example, methyl, ethyl, propyl, dimethylaminopropyl, isobutyl, butyl.

The hydroxy groups $R_3$ and those in W can be functionally modified, for example by etherification or esterification, the free or modified hydroxy groups in W being in the $\alpha$-position, free hydroxy groups being preferred. Suitable ether and acyl residues are the residues known to persons skilled in the art. Ether residues that can be readily split off are preferred, such as, for example, the tetrahydropyranyl, tetrahydrofuranyl, $\alpha$-ethoxyethyl, trimethylsilyl, dimethyl-tertbutylsilyl and tribenzylsilyl residue. Examples for acyl residues are: acetyl, propionyl, butyryl, benzoyl.

Straight- and branched-chain, saturated alkyl residues of 1–7 carbon atoms are suitable as the alkyl group $R_2$ Examples are methyl, ethyl, propyl, butyl and isobutyl, tert-butyl, pentyl, hexyl, heptyl.

Suitable alkylene groups D are straight-chain or branched-chain, saturated ones of up to 5 carbon atoms. Examples that can be cited are methylene, ethylene, 1,2-propylene, ethylethylene, trimethylene, tetramethylene, pentamethylene, 1-methyltetramethylene, 1-methyltrimethylene.

Inorganic and organic bases such as known to a person skilled in the art for the formation of physiologically compatible salts are suitable for salt formation with the free acids ($R_1=H$). Examples are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The preparation of the compounds of Formula I is described in detail in EP 2,234 and EP 11,591.

The following pharmacological properties are described for the carbacyclin derivatives of Formula I in EP 11,591: lowering of peripheral arterial and coronary vascular resistance, inhibition of thrombocyte aggregation and dissolution of platelet thrombi, myocardial cytoprotection; lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, therapy for shock, inhibition of bronchoconstriction, inhibition of gastric acid secretion and cytoprotection of gastric and intestinal mucosa; aniallergic properties, lowering of pulmonary vascular resistance and of pulmonary blood pressure, promotion of kidney blood flow, utilization in place of heparin or as adjuvant in dialysis or hemofiltration, preservation of blood plasma stores, especially of stored blood platelets, inhibition of labor, treatment of gestational toxicosis, enhancement of cerebral blood flow, and antiproliferation.

Cytoprotection of liver, pancreas and kidney has not been described and has no direct connection, either, with the cytoprotection features described in EP 11,591. The compounds of Formula I are furthermore suitable for the treatment of organs to be transplanted.

Therapy of acute pancreatitis by medicaments, heretofore customary, is based on the use of enzyme inhibitors, such as aprotinin which is to prevent formation of kinins and thus grave shock symptoms by inactivation of kallikrein released from the destroyed pancreas tissue. Aprotinin is furthermore to protect the pancreas from self digestion by backed up trypsin. In recent times, various hormones have been utilized in pancreatitis therapy, such as somatostatin, glucagon or calcitonin, thought to inhibit secretory processes.

Although both forms of therapy possess evident effects—for example, they inhibit pathological passage of amylase into the bloodstream—they have not been able, in the final analysis, to reduce the mortality in grave disease cases.

It has now been found in studies on an animal model considered relevant for human pancreatitis that the prostacyclin derivatives of Formula I exhibit protective activity, which was completely surprising and unexpected from their heretofore known profile of effectiveness. Observations include a reduction in amylase concentration in the serum, normalization of the morphological picture of a damaged pancreas, a marked decrease in accumulation of fluid as a consequence of pancreatitis in the peritoneal cavity (ascites), and a generally more rapidly progressing healing action.

The prostacyclin derivatives of general Formula I also exhibit surprisingly cytoprotective effects in the liver and kidney. For the liver, such an effect could be demonstrated with prostacyclin derivatives of Formula I in an unexpectedly low dose on a cell culture of hepatic cells against damage by carbon tetrachloride. For the kidney, the cytoprotective effect could be confirmed in the form of a protective activity against induction of papillary necroses due to nonsteroidal anti-inflammatory agents.

The dosage of the compounds is 1–1,500 $\mu$g/kg/day if administered to human patients. The unit dosage for the pharmaceutically acceptable carrier is 0.01–100 mg.

The dosage for an i.v. administration as a long-term infusion in conventional aqueous solvents, e.g. 0.9% strength NaCl solution, is preferably in doses of between 0.1 ng/kg/min and 0.1 $\mu$g/kg/min.

Accordingly, the invention also concerns medicinal agents based on the compounds of general Formula I and conventional auxiliary agents and excipients.

The active compounds of this invention are to serve, in conjunction with the auxiliary agents known and customary in galenic pharmacy, for example for the preparation of cytoprotective agents.

The invention also relates to a process for the preparation of the agents of this invention, characterized by conventionally bringing the cytoprotectively active compounds of Formula I into a galenic formulation with the conventional auxiliary agents and excipients.

EXAMPLE 1

Experimental pancreatitis is triggered by overstimulation of the pancreas with a peptide, caerulein, equivalent in its effect to the hormone cholecystokinin responsible for controlling exocrine pancreas secretion (Virchows Arch. A 382:31–47, 1979, and Cell Tis. Res. 194:447–462, 1978). Whereas intravenous feeding of a low dose of caerulein (e.g. 0.5 $\mu$g/kg/min) stimulates secretion of pancreatic juice as after ingestion of food, with an increase in the activity of all processes participating herein, from protein synthesis in the pancreatic cells by way of intracellular transport of the thus-formed enzymes up to their apical secretion into the lumina of the pancreatic lobules (acini) connected to the pancreatic duct system, pathological changes occur with administration of higher doses (5 $\mu$g/kg/min). Pancreas secretion is drastically reduced; the organ swells due to water inclusions between the cells (interstitial edema), the enzymes formed are no longer released into the duct system but rather toward the side into the interstitial space or are accumulated in large cavities (vacuoles) within the cells themselves (Dig. Dis. Sci. 27:993–1002, 1982). At the same time, there is an increase in the activity of cell-dissolving (=lysosomal) enzymes in the tissue (Dig. Dis. Sci. 28:923, 1983), ascites occurs, and amylase activity in the blood rises. After induction of pancreatitis, fatty necroses are found in the pancreas, along with a pronounced cellular inflammation reaction. This array of symptoms entirely corresponds in all details to the picture of acute pancreatitis in man.

The protective effect of the prostacyclins of Formula I can be very effectively demonstrated by means of two selected compounds, iloprost and nileprost, Iloprost Nileprost by administering these compounds to rats by intravenous infusion for a certain time period in doses of 0.1 or 0.5 μg/kg/min, followed by a long-term i.v. infusion of caerulein in a strongly pancreatitis-inducing dose (5 μg/kg/h). Table 1 shows the results of this experiment, wherein the amylase activity in the serum was measured and indicated in the dimension of units/liter (U/l) and the vacuolization of the cells of the exocrine pancreas, the occurrence of ascites, and the enlargement of the pancreas by interstitial edema was evaluated by scoring.

By means of i.v. infusion, serum amylase was reduced in case of iloprost as well as nileprost to half the level that had been raised under caerulein and the occurrence of ascites was completely prevented. Iloprost also effected drastic reduction of vacuolization and edema formation. Nileprost likewise showed this effect, through in part not quite so strongly pronounced.

TABLE 1

Effect of the Prostacyclins Iloprost and Nileprost on Induction of Pancreatitis in Rats Created by Intraveneous Infusion of Caerulein

| Treatment | | Dose | n | Edema | Ascites | Vacuoles | Serum Amylase (U/l) |
|---|---|---|---|---|---|---|---|
| 1. | | | | | | | |
| 2. Caerulein | (3 h) | 5 μg/kg/h | 20 | +++ | +++ | +++ | 80.0 ± 5.2 |
| 1. Iloprost | (3 h) | 0.1 μg/kg/min | 8 | + | − | + | 37.4 ± 16.5 |
| 2. Caerulein | (3 h) | 5 μg/kg/h | | | | | |
| 1. Iloprost | (3 h) | 0.5 μg/kg/min | 6 | + | − | + | 48.2 ± 18.2 |
| 2. Caerulein | (3 h) | 5 μg/kg/h | | | | | |
| 1. Nileprost | (3 h) | 0.1 μg/kg/min | 6 | ++ | − | + | 48.4 ± 16.3 |
| 2. Caerulein | (3 h) | 5 μg/kg/h | | | | | |
| 1. Nileprost | (3 h) | 0.5 μg/kg/min | 6 | ++ | − | ++ | 57.8 ± 9.2 |
| 2. Caerulein | (3 h) | 5 μg/kg/h | | | | | |

− no pathological change
+ slight pathological change
++ medium pathological change
+++ grave pathological change

EXAMPLE 2

For testing the cytoprotective effect of the novel prostacyclin derivatives on liver cells, rat liver cells cultivated in isolated fashion were utilized, these cells having been poisoned with carbon tetrachloride ($CCl_4$) to produce defined cell damage. For determining cell damage, three different parameters were employed: 1. Evaluation of cell morphology under a light microscope; 2. Uptake of the dye trypan blue, a compound which is selectively enriched in necrotic cells; 3. Release of cytoplasmic enzymes into the surrounding medium due to destruction of cell membrane; the activity of lactate dehydrogenase (LDH) was measured.

Cell Culture: One week prior to cell preparation, the test animals (rats, ♀, 140–160 g) were treated with phenobarbital (50 mg/kg/day). The liver cells (hepatocytes) were isolated by perfusion with collagenase analogously to the method by Seglen (Methods in Cell Biology 13 : 29, 1976) and disseminated in collagen-coated plastic dishes in Williams medium E in a density of $5 \times 10^4$ cells/$cm^2$.

Testing Scheme: After an attachment period of 12 minutes, the cultures were washed in order to remove dead cells. $CCl_4$ (0.12 and 0.35 μl/ml, respectively) was introduced in an alcoholic solution into the medium. The compound of Formula I to be tested was added in the concentrations indicated in the legends for the following FIGS. 1-3.

For determining trypan blue uptake, trypan blue (final concentration 0.02%) was added to the medium. The number of cells stained blue was determined by counting out 1,200–1,500 hepatocytes per culture and expressed in percent of cells counted in total ("trypan blue index"). For determining lactate dehydrogenase (LDH) release, an aliquot was taken from the medium at the end of the test. Thereafter the membrane of the still intact cells was destroyed by addition of triton (final concentration 1%) in order to determine the LDH activity present in total in the culture. The LDH activity measured before triton addition was expressed in percent of total LDH activity of the culture. The measurement of LDH activity took place according to Bergmeyer (Methoden der enzymatischen Analyse [Methods of Enzymatic Analysis], Chemie Publishers, Weinheim, 1970).

The cytoprotective activity of the compounds of Formula I in the liver was confirmed by using iloprost as example.

2(a) Cell Morphology

Figure 1A:
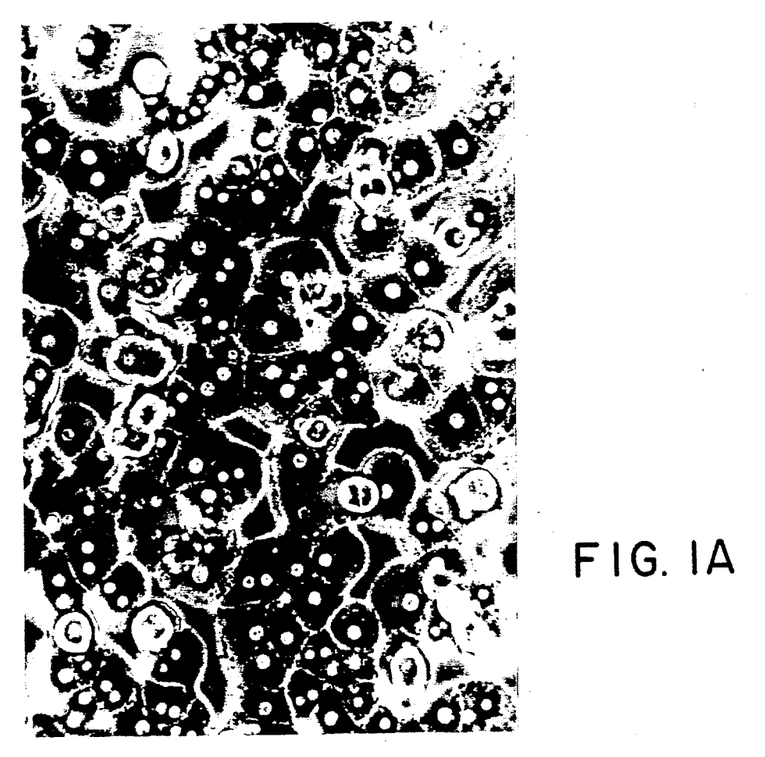
Figure 1B:
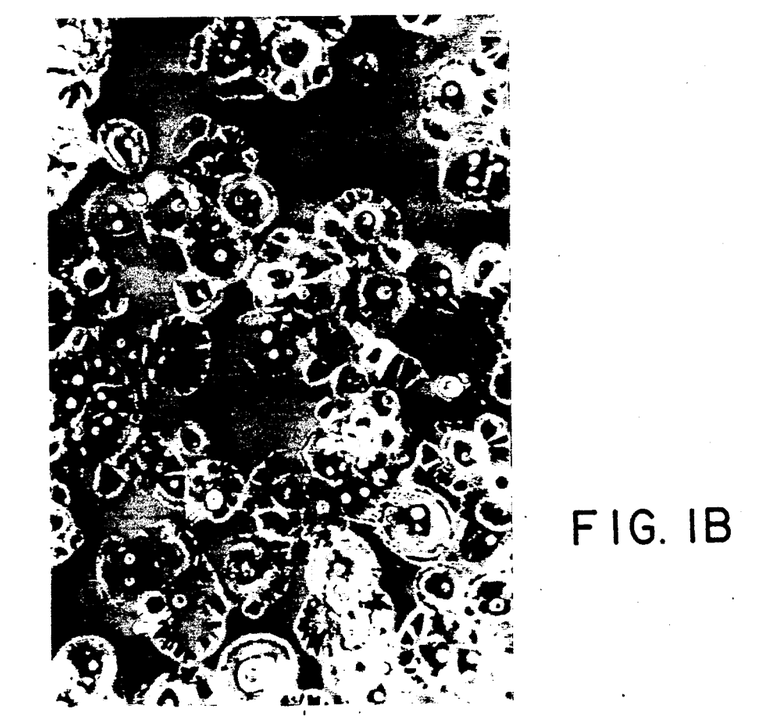
Figure 1C:
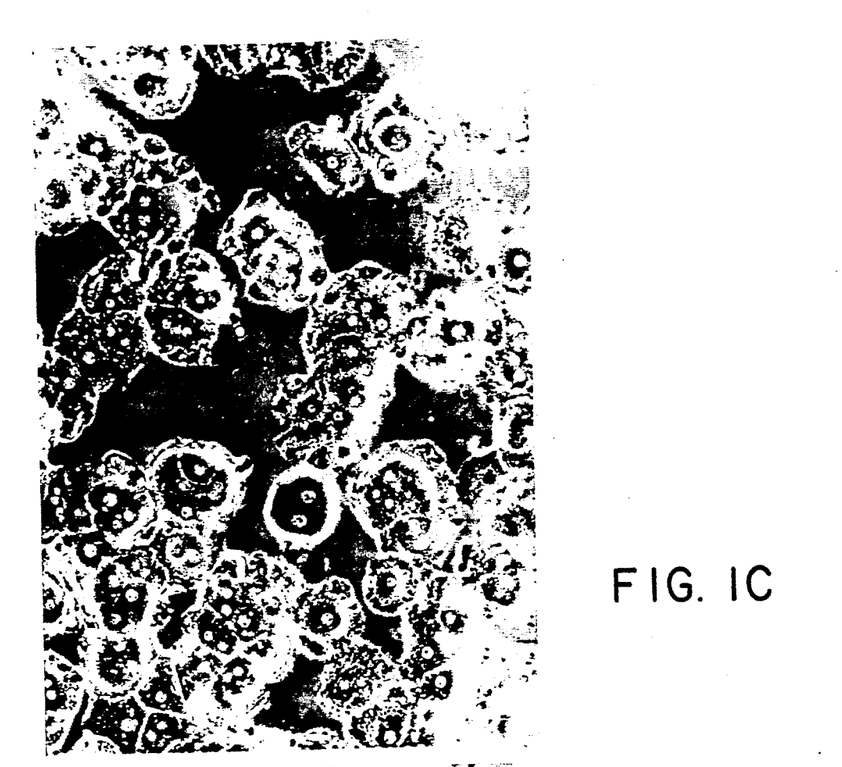
Figure 1D:
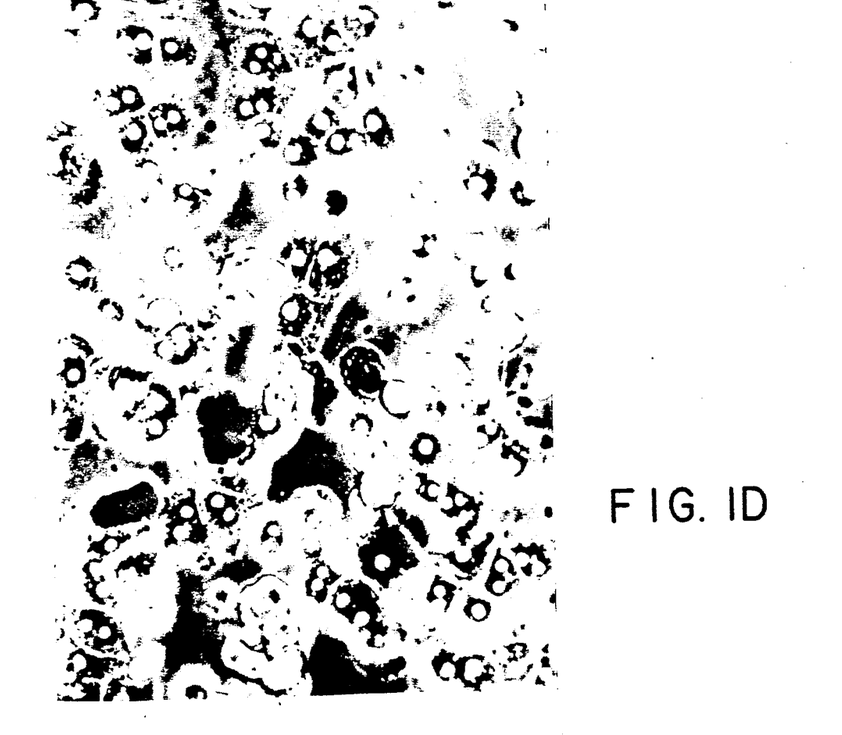
Figure 1E:
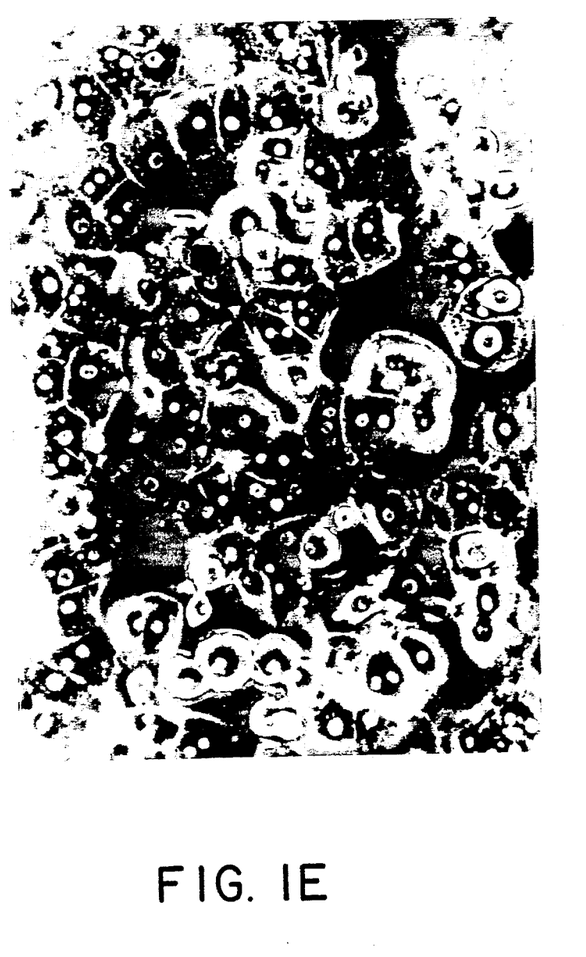

Under observation by light microscope, the cultivated cells exhibited the trabecular arrangement typical for hepatocytes, a relatively homogeneous cytoplasm, and clearly visible, well preserved cell membranes (FIG. 1a). After poisoning with $CCl_4$, many hepatocytes appeared granulated; the membrane of the cells showed numerous diverticula of varying shapes (FIGS. 1b, c). In several cells, the membrane could no longer be recognized; other cells had disintegrated into various parts (FIG. 1c, arrows). In the case where iloprost was added to the medium simultaneously with $CCl_4$, the above-described symptoms of poisoning were practically completely absent (FIGS. 1d, e) so that the cells could hardly be distinguished from those in untreated cultures.

2(b) Trypan Blue Uptake

Figure 2:
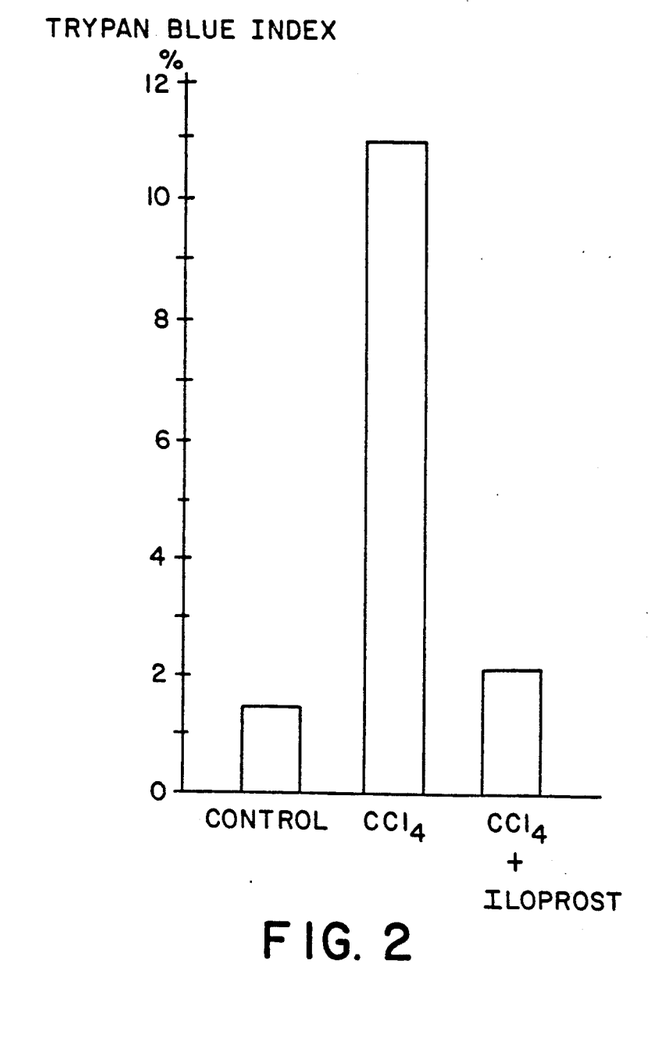
FIG. 2 is a graph illustrating Trypan Blue Index determinations 1.5 hours after the addition of $CCl_4$ and, respectively addition of $CCl_4$ plus Iloprost.

The proportion of cells taking up trypan blue was determined to find the number of cells that died after the effect of CCl$_4$. FIG. 2 shows the result of a representative experiment. The addition of CCl$_4$ causes an approximately eightfold increase in the trypan blue index; this rise can be extensively prevented by the addition of iloprost.

2(c) Release of Lactate Dehydrogenase (LDH)

Figure 3:
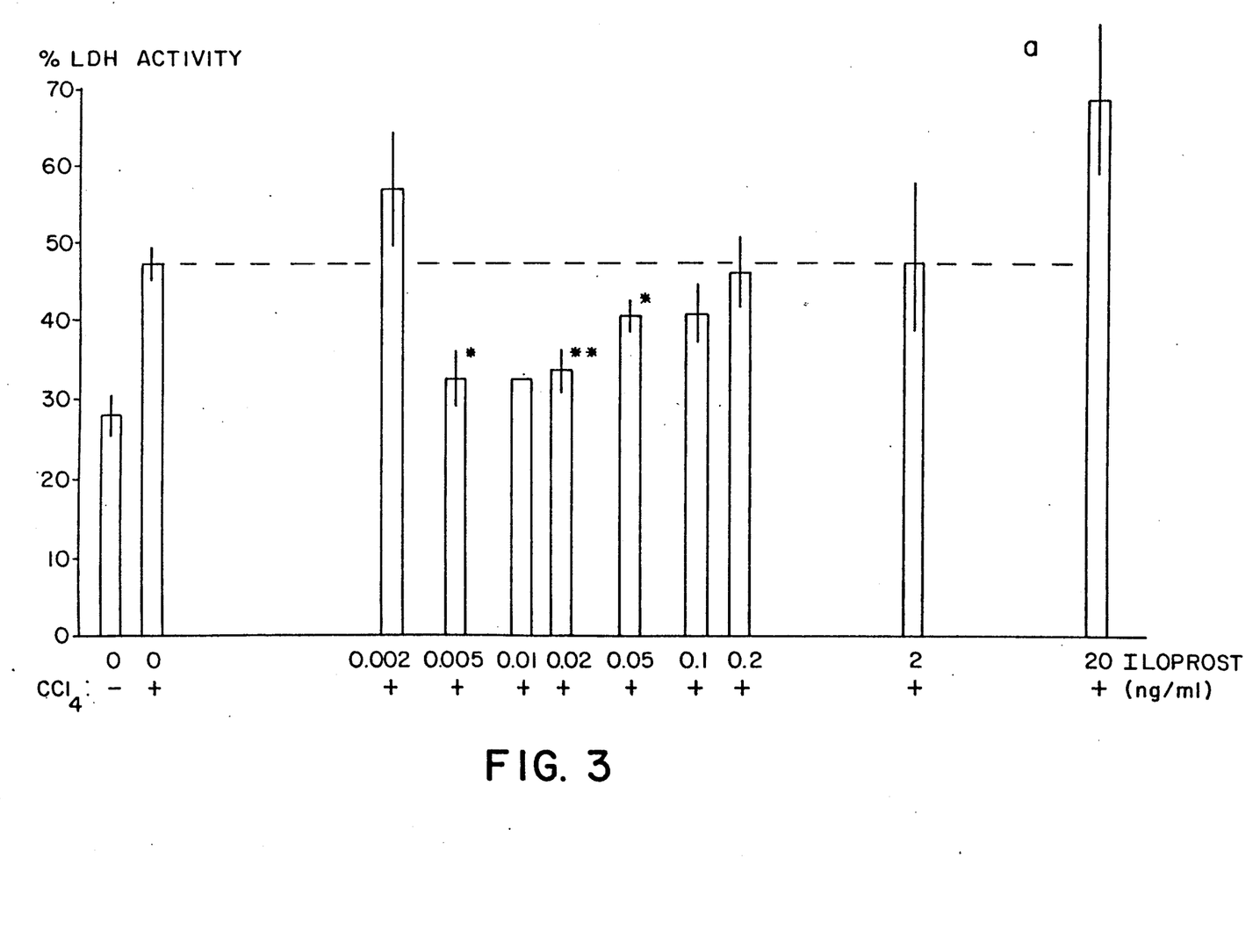
FIG. 3 is a graph illustrating lactate dehydrogenase (LDH) activity in the medium wherein the effect of Iloprost on LDH release is shown after $CCl_4$ addition (0.35 $\mu l/ml$) Iloprost was added in aqueous solution 20 minutes before $CCl_4$ intoxication. Statistical comparison: cultures treated with Iloprost were compared with $CCl_4$-poisoned cultures.
Figure 4:
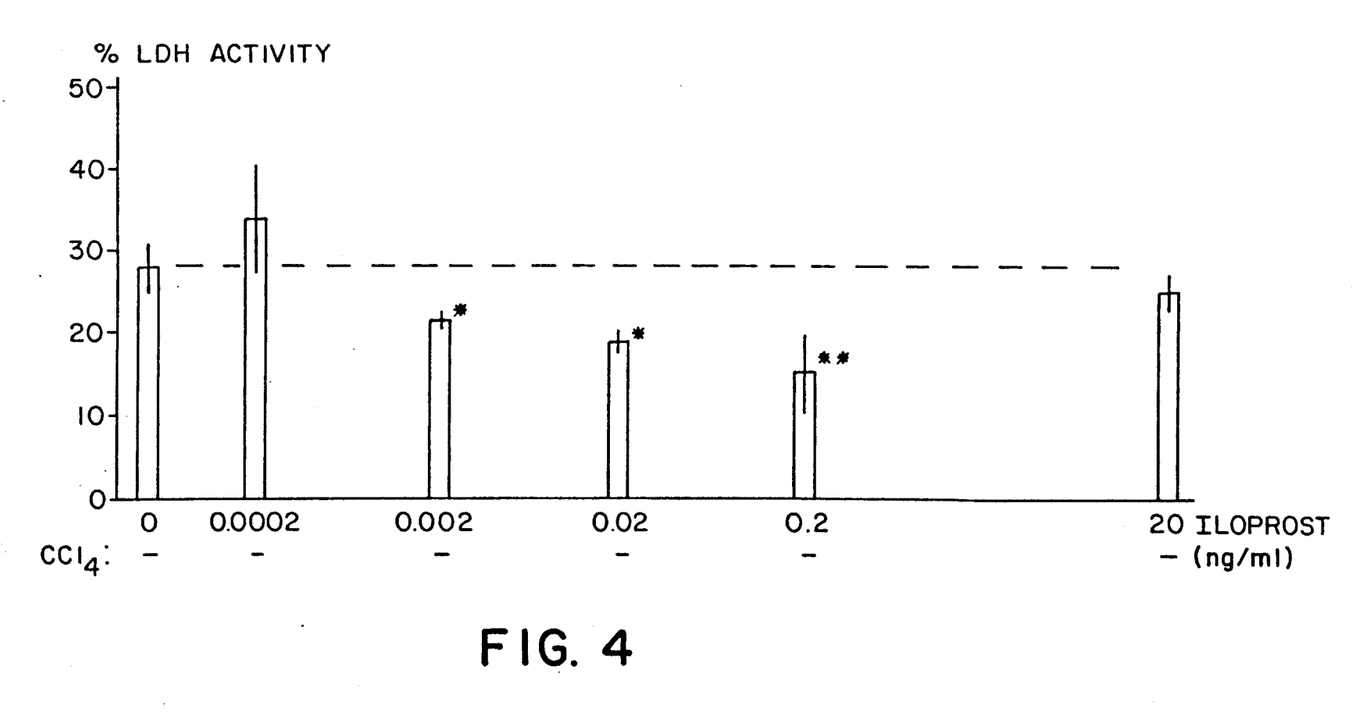
FIG. 4 is a graph similar to FIG. 3 illustrating the effect of Iloprost on LDH Release in control cultures. Statistical comparison: cultures treated with Iloprost were compared with untreated cultures.

Treatment of the cultures with CCl$_4$ brings about an approximate doubling of LDH activity in the medium (FIG. 3a) admitting the conclusion that the cell membranes have been destroyed. This increase was almost entirely suppressed by iloprost concentrations of 0.005 to 0.02 ng/ml; 0.05 and 0.1 ng/ml partially prevented the increase. Also when adding iloprost to cell cultures not poisoned with CCl$_4$, a marked drop in LDH activity released into the medium could be observed (FIG. 3b). Apparently, membrane damage occurs in the cultivated cells also without CCl$_4$ addition; such damage can likewise be mitigated by iloprost. Consequently, the protective action of iloprost is not restricted to the consequences of CCl$_4$ poisoning.

2(d) It can be seen from these observations that iloprost has a cytoprotective effect on liver cells. This final conclusion is based on the detection of three independent parameters:

Preservation of cell morphology, i.e. no appearance of microscopically visible damage to the cell membrane, Prevention of cell necrosis, measured by means of the trypan blue index, and Prevention of release of cell plasma components into the surrounding medium, measured by means of lactate dehydrogenase release.

The doses providing cytoprotective activity range from 0.005 to 0.2 ng/ml.

EXAMPLE 3

| | | Galenic Preparation |
|---|---|---|
| | 0.5 mg | 5-[(E)-(1S,5S,6R,7R)-7-Hydroxy-6-[(E)-(4RS)-3α-hydroxy-4-methyl-oct-1-en-6-ynyl]bicyclo[3.3.0]octan-3-ylidene]pentanoic acid |
| | 1.212 mg | Tris buffer |
| ad | pH 8.3 | 0.1N Hydrochloric acid |
| | 8.9 mg | NaCl |
| | 0.01 ml | 96% Strength ethanol |
| ad | 1.0 ml | for injection purposes |

We claim:

1. A method of preventing or treating damage to the kidney of a patient in need of such prevention or treatment, comprising administering to the patient an effective amount of nileprost.

2. A method of claim 1, which is also for preventing or treating damage to the liver or pancreas.

3. A method preventing or treating damage to the kidney of a patient in need of such prevent or treatment, comprising administering to the patient an effective amount of iloprost.

4. A method of claim 3, which is also for preventing or treating damage to the liver or pancreas.

* * * * *